United States Patent
Charles

(10) Patent No.: US 11,259,960 B2
(45) Date of Patent: Mar. 1, 2022

(54) SURGICAL INSTRUMENT USING DETECTED LIGHT

(71) Applicant: Novartis AG, Basel (CH)

(72) Inventor: Steven T. Charles, Germantown, TN (US)

(73) Assignee: Alcon Inc., Fribourg (CH)

( * ) Notice: Subject to any disclaimer, the term of this patent is extended or adjusted under 35 U.S.C. 154(b) by 100 days.

(21) Appl. No.: 16/270,895

(22) Filed: Feb. 8, 2019

(65) Prior Publication Data

US 2019/0254868 A1    Aug. 22, 2019

Related U.S. Application Data

(60) Provisional application No. 62/633,866, filed on Feb. 22, 2018.

(51) Int. Cl.

| | |
|---|---|
| *A61F 9/007* | (2006.01) |
| *A61B 17/34* | (2006.01) |
| *A61B 90/90* | (2016.01) |
| *A61B 90/96* | (2016.01) |
| *A61B 90/92* | (2016.01) |
| *A61B 17/00* | (2006.01) |
| *A61B 90/00* | (2016.01) |

(52) U.S. Cl.
CPC .......... *A61F 9/007* (2013.01); *A61B 17/3421* (2013.01); *A61B 90/90* (2016.02); *A61B 90/92* (2016.02); *A61B 90/96* (2016.02); *A61B 2017/00057* (2013.01); *A61B 2017/00119* (2013.01); *A61B 2017/00907* (2013.01); *A61B 2090/373* (2016.02)

(58) Field of Classification Search
CPC ......... A61F 9/007; A61B 90/90; A61B 90/96; A61B 90/92; A61B 17/3421; A61B 2017/00907; A61B 2090/373; A61B 2017/00119; A61B 2017/00057; G02B 6/24; G02B 6/00; G05B 2219/39002
See application file for complete search history.

(56) References Cited

U.S. PATENT DOCUMENTS

| 5,651,783 A | 7/1997 | Raynard |
|---|---|---|
| 7,934,648 B2 | 5/2011 | Charles et al. |
| (Continued) | | |

FOREIGN PATENT DOCUMENTS

WO    WO2014159889 A1    10/2014

*Primary Examiner* — Gary Jackson
*Assistant Examiner* — Sebastian X Lukjan

(57) ABSTRACT

Various embodiments are generally directed to a surgical instrument for detecting light, such as by measuring light traveling in a waveguide, for instance. Some embodiments are particularly directed to a determining one or more parameters associated with ocular surgery based on detection of the light. In one or more embodiments, for example, a surgical instrument may include a cannula, a waveguide, a transducer, and logic implemented in circuitry communicatively coupled with the transducer. In one or more such embodiments, the cannula may comprise at least a portion of the waveguide. In some embodiments, the transducer may detect light traveling in a first direction in the waveguide. In some such embodiments, the logic may determine at least one parameter associated with ocular surgery based on the light detected by the transducer.

12 Claims, 6 Drawing Sheets

(56) References Cited

U.S. PATENT DOCUMENTS

| | | | |
|---|---|---|---|
| 8,315,280 B2 | 11/2012 | Zimare | |
| 8,485,972 B2 | 7/2013 | Papac et al. | |
| 8,892,191 B2 | 11/2014 | Brennan | |
| 9,597,009 B2 | 3/2017 | Ren | |
| 9,693,686 B2 | 7/2017 | Smith | |
| 9,839,749 B2 | 12/2017 | Johnson | |
| 10,039,669 B2 | 8/2018 | Heeren | |
| 10,238,543 B2 | 3/2019 | Farley | |
| 10,244,931 B2 | 4/2019 | Kern | |
| 10,285,584 B2 | 5/2019 | Charles | |
| 10,292,783 B2 | 5/2019 | Bacher | |
| 10,307,290 B2 | 6/2019 | Kern | |
| 10,398,307 B2 | 9/2019 | Charles | |
| 2011/0118729 A1 | 5/2011 | Heeren | |
| 2011/0295240 A1* | 12/2011 | Hamel | A61M 25/0017 604/544 |
| 2012/0209257 A1* | 8/2012 | van der Weide | A61B 18/1815 606/23 |
| 2012/0265184 A1* | 10/2012 | Sliwa | A61B 5/0036 606/15 |
| 2016/0128547 A1* | 5/2016 | Ogawa | A61B 1/00055 600/107 |
| 2017/0045721 A1 | 2/2017 | Charles | |
| 2017/0086906 A1* | 3/2017 | Tsuruta | A61B 18/10 |
| 2017/0172667 A1 | 6/2017 | Charles | |
| 2018/0132963 A1 | 5/2018 | Diao | |
| 2018/0338776 A1 | 11/2018 | Farley | |
| 2019/0110682 A1 | 4/2019 | Charles | |
| 2019/0110862 A1 | 4/2019 | Anderson | |
| 2019/0209372 A1 | 7/2019 | Farley | |

* cited by examiner

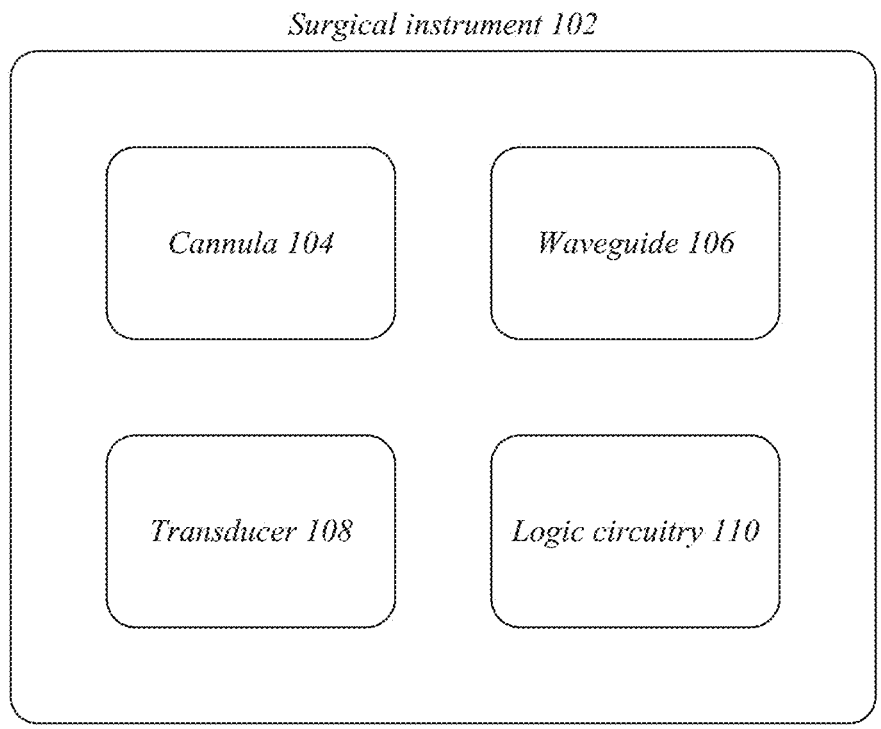

400A

400B

SURGICAL INSTRUMENT USING DETECTED LIGHT

PRIORITY CLAIM

This application claims the benefit of priority of U.S. Provisional Patent Application Ser. No. 62/633,866 titled "Surgical Instrument Using Detected Light," filed on Feb. 22, 2018, whose inventor is Steven T. Charles, which is hereby incorporated by reference in its entirety as though fully and completely set forth herein.

BACKGROUND

Generally, surgical instruments include one or more tools or devices designed to perform specific actions or functions involved in carrying out desired effects during surgery or operations. Cannulas are typically a tubular type of surgical device used to gain access to an intended space. Oftentimes, cannulas are used in ophthalmic or ocular surgery, which may include performing an operation on an eye or its adnexa. Further, these surgeries may include operations on the inside of the eye. Accordingly, a cannula may be used to provide access to the inside of the eye during an ophthalmic surgery. In various embodiments, ophthalmic surgery may be performed on a patient for therapeutic purposes.

BRIEF DESCRIPTION OF THE DRAWINGS

FIG. 1 illustrates an exemplary surgical instrument according to one or more embodiments described herein.

DETAILED DESCRIPTION

Figure 2A:
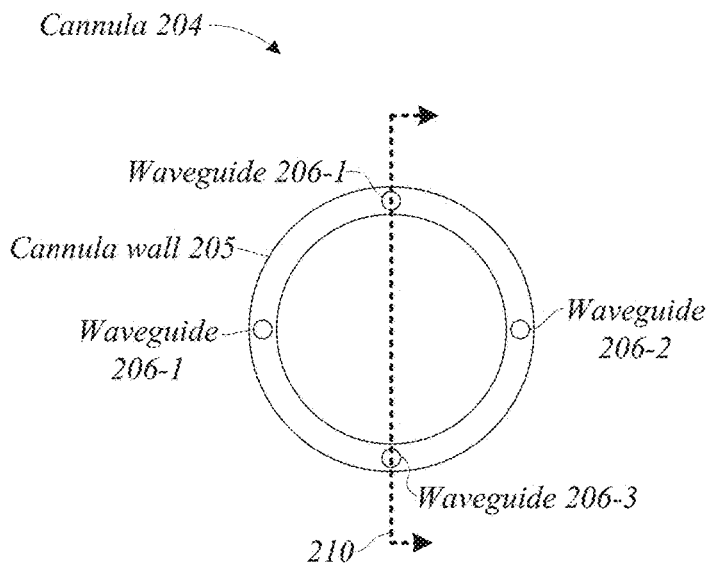
FIGS. 2A-2B illustrate an exemplary cannula according to one or more embodiments described herein.

Various embodiments are generally directed to a surgical instrument for detecting light, such as by measuring light traveling in a waveguide, for instance. Some embodiments are particularly directed to a determining one or more parameters associated with ocular surgery based on detection of the light. In one or more embodiments, for example, a surgical instrument may include a cannula, a waveguide, a transducer, and logic implemented in circuitry communicatively coupled with the transducer. In one or more such embodiments, the cannula may comprise at least a portion of the waveguide. In some embodiments, the transducer may detect light traveling in a first direction in the waveguide. In some such embodiments, the logic may determine at least one parameter associated with ocular surgery based on the light detected by the transducer. For instance, the parameter associated with ocular surgery may include one or more of whether the instrument or cannula is located inside an eye, a position of the instrument or cannula inside an eye, whether a second instrument is located inside an eye, a position of the second instrument inside an eye, an identity of a second instrument inserted into the eye, and an amount of illumination within an eye.

Some challenges facing surgical instruments include devices that are inefficient, dangerous, and have limited capabilities. These challenges may result from surgical instruments requiring manual inspection and/or estimation to determine one or more parameters associated with ocular surgery. For instance, determining whether an infusion cannula is located inside an eye may require manual inspection, leading to safety issues. In such instances, for example, the infusion cannula may be located in a supra-choroidal space (e.g., between the choroid and sclera of an eye) instead of inside the eye. In such examples, inadvertent infusion into the supra-choroidal space can lead to complications in ocular surgery, such as by inflating the choroid with fluid that pushes the choroid and the retina into the center of the eye, stretching blood vessels and causing supra-choroidal hemorrhaging. Manual inspection can be further complicated when an eye has a low initial intraocular pressure. Additionally, even if the cannula is initially positioned properly within the eye, inadvertent pulling may unintentionally remove the cannula from the proper position within the eye. Adding further complexity, it may be difficult and/or inconvenient to identify a tool and/or determine whether a tool inserted into the cannula is properly located inside an eye. For instance, a tool may be too small to manually inspect to determine the type of the tool. In some embodiments, tools may only be identified by connecting them to a console, resulting in unnecessary inconvenience. These and other factors may result in undesirable surgical instruments with limited flexibility, deficient performance, and safety concerns. Such limitations can reduce the capabilities, usability, and applicability of the surgical instrument, contributing to inefficient devices with limited abilities.

Various embodiments described herein include a surgical instrument that can determine one or more parameters associated with an ocular surgery through the detection of light. For example, the detection of light reflected off a tool inserted into the cannula may be used to identify the tool or determine a position of the tool. In such examples, the tool may include markings, such as a bar code or stripes, to enable the surgical instrument to identify the tool or determine the position of the tool based on the detection of light reflected off the tool. In some embodiments, the tool may not have markings, but instead, the general reflectivity of the tool surface may be detected (e.g., which may depend on the tool surface material, finish, color, etc.) Different levels of detected reflected light may be correlated to different tool types. In another example, the detection of light may enable the surgical instrument to determine an amount of illumination or light, such as within an eye. In one or more embodiments, the surgical instrument may determine one or more parameters regarding surgical tools utilized therewith, such as identification, number, or location (e.g., whether inside or outside of eye). In one or more such embodiments, mode switching, tool activation/arming may occur based on the location/configuration of a tool, such as to promote safety and efficiency.

In some embodiments, the surgical instrument may continually monitor an amount of light detected. In various embodiments, determining and/or monitoring the amount of light detected may provide safety advantages. For instance, if an amount of illumination within the eye exceeds a safety threshold (e.g., phototoxicity level), the surgical instrument may generate an alert and/or reduce the amount of illumination. In another instance, the surgical instrument may determine whether an infusion cannula is located inside an eye. In such other instance, the surgical instrument may prevent infusion unless the infusion cannula is properly located inside the eye. In various embodiments, the surgical instrument may sum the light from multiple sources (e.g., chandelier, endoilluminator, and/or illuminated tools). In various such embodiments, knowing the total fluence may enable valuable safety measures. In these and other ways one or more of the surgical instruments described herein may function in a safe, efficient, and novel manner to achieve better performing surgical instruments, resulting in several technical effects and advantages.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well-known structures and devices are shown in block diagram form in order to facilitate a description thereof. The intention is to cover all modification, equivalents, and alternatives within the scope of the claims.

FIG. 1 illustrates an embodiment of an operating environment 100 that may be representative of various embodiments. Operating environment 100 may include surgical instrument 102. In many embodiments, the surgical instrument 102 may include a cannula 104, a waveguide 106, a transducer 108, and logic circuitry 110. In one or more embodiments described herein, the surgical instrument may determine one or more parameters associated with ocular or ophthalmic surgery based on light. For instance, transducer 108 may detect light traveling within waveguide 106, and logic circuitry 110 may determine one or more parameters associated with ocular surgery based on the light detected by the transducer 108. In such instances, cannula 104 may include at least a portion of waveguide 106 such that light may enter waveguide 106 proximate cannula 104. Embodiments are not limited in this context.

In one or more embodiments, surgical instrument 102 may be used in ocular surgery, such as vitreoretinal surgery. As previously mentioned, in many embodiments, cannula 104 may include at least a portion of waveguide 106. For instance, the portion of waveguide 106 may be coupled to or embedded in cannula 104. In some embodiments, including a portion of waveguide 106, such as an end of the waveguide 106, may enable light to enter and/or exit waveguide 106 proximate cannula 104. In various embodiments, surgical instrument 102 may include a light source to generate the light detected by transducer 108. For example, the light source may generate light that exits waveguide 106 proximate cannula 104 (e.g., on the exterior of cannula 104 or on the interior of cannula 104). In some examples, transducer 108 may detect light that exits waveguide 106 and is reflected such that it enters waveguide 106. In some examples, light may enter waveguide 106 from other sources, such as an operating microscope. In various embodiments, surgical instrument 102 described herein may have any number/configuration of waveguides 106 to achieve one or more functionalities described herein.

In various embodiments, enabling light to enter waveguide 106 proximate cannula 104 may allow transducer 108 to detect light in a space that cannula 104 is utilized to gain access to. For instance, transducer 108 may detect light on the inside of an eye. In some embodiments, enabling light to enter waveguide 106 proximate cannula 104 may allow transducer 108 to detect light within cannula 104. For example, transducer 108 may detect light reflected from a tool inserted within cannula 104. In one or more embodiments, enabling light to exit waveguide 106 proximate cannula 104 may allow cannula 104 to serve as an illuminator. For instance, cannula 104 may be used to illuminate the inside of an eye. In various embodiments, enabling light to exit waveguide 106 proximate cannula 104 may allow tools inserted into cannula 104 to be scanned. For instance, markings, such as a bar code, on a tool may be scanned. In some embodiments, the tool may not have markings, but instead, the general reflectivity of the tool surface may be detected (e.g., which may depend on the tool surface material, finish, color, etc.) Different levels of detected reflected light may be correlated to different tool types.

In some embodiments, logic circuitry 110 may determine one or more parameters associated with ocular surgery based on the light detected by transducer 108. In various embodiments, the one or more parameters associated with ocular surgery may include one or more of whether the cannula 104 is located inside an eye, a position of the cannula 104 inside the eye, whether a tool is located inside the eye, a position of the tool inside the eye, an identity of a tool inserted into the cannula 104, and an amount of illumination within the eye. For example, the detection of light reflected off markings on a tool inserted into the cannula 104 may be used to identify the tool or determine a position of the tool. In such examples, the tool may include markings, such as a bar code or position gauge, to enable logic circuitry 110 to identify the tool or determine the position of the tool based on the detection of light reflected off the tool by transducer 108. In some embodiments, the markings may be opaque (and, for example, the rest of the tool surface is more reflective than the markings) or the markings may be reflective (and, for example, the rest of the tool surface be not as reflective). Relative levels of reflected light may be associated with different marking types. For example, markings including ten opaque lines will result in less reflected light than markings with 5 lines (of similar thickness as the ten opaque lines). In some embodiments, the tool may not have markings, but instead, the general reflectivity of the tool surface may be detected (e.g., which may depend on the tool surface material, finish, color, etc.) Different levels of detected reflected light may be correlated to different tool types.

In another example, the detection of light may enable the surgical instrument 102 to determine an amount of illumination or light, such as within an eye. In some embodiments, the surgical instrument 102 may continually monitor an amount of light detected. In various embodiments, determining and/or monitoring the amount of light detected may provide safety advantages. For instance, if an amount of illumination within the eye exceeds a safety threshold, logic circuitry 110 may generate an alert and/or reduce the amount of illumination. In another instance, logic circuitry 110 may determine whether an infusion cannula is located inside an eye. In such other instance, logic circuitry 110 may prevent infusion unless the infusion cannula is properly located inside the eye.

More generally, in some embodiments, cannula 104 may include a tubular type of surgical device used to gain access to an intended space. For instance, a cannula may be used to gain and/or provide access to the inside of the eye during an ophthalmic surgery. In some embodiments, cannula 104 may include a tube that is inserted into a vein or body cavity to administer medicine, drain off fluid, and/or insert a surgical tool. In one or more embodiments described herein, cannula 104 may include one or more portions of waveguide 106, transducer 108, and logic circuitry 110.

In many embodiments, waveguide 106 may provide a path for light to travel between cannula 104 and transducer 108. In some embodiments, waveguide 106 may provide a path from light to travel between a light source and cannula 104. In various embodiments, waveguide 106 may include one or more waveguides. For instance, waveguide 106 may include one or more optical fibers, such as an illumination nanofibers. In various such embodiments, each of the one or more waveguides comprised in waveguide 106 may include an independent light path. Some embodiments described herein may include a beam splitter to separate light in waveguide 106 that exits proximate cannula 104 from light that enters proximate cannula 104, such as when waveguide 106 includes a common light path for light entering and exiting proximate cannula 104. In other embodiments described herein, waveguide 106 may include independent light paths for transducer 108 and a light source.

In one or more embodiments, waveguide 106 may include one or more waveguides that terminate on the exterior (e.g., at the end) of cannula 104 and/or one or more waveguides that terminate on the interior of cannula 104. In one or more such embodiments, waveguides that terminate on the exterior of cannula 104 may be used for determining parameters associated with an environment or location of the cannula 104 (e.g., ambient light). Additionally, or alternatively, in one or more such embodiments, waveguides that terminate on the interior of cannula 104 may be used for determining parameters associated with a tool inserted into cannula 104.

In some embodiments, transducer 108 may include any device that converts light into a proportional electrical signal. In some such embodiments, the proportional electrical signal may be utilized by logic circuitry 110 to determine one or more parameters associated with ocular surgery. In some embodiments, transducer 108 may include one or more transducers and/or one or more channels. For example, in embodiments in which waveguide 106 includes multiple waveguides with independent light paths, transducer 108 may include a separate transducer for each light path. In another example, transducer 108 may include a separate channel for each light path. In yet another example, two or more of the independent light paths may be recombined into a common waveguide before being detected by transducer 108. In many embodiments, transducer 108 may be communicatively coupled with logic circuitry 110. In many such embodiments, logic circuitry 110 may receive signals from transducer 108 that enable logic circuitry to determine and/or monitor light detected by transducer 108.

In various embodiments, logic circuitry 110 may implement or execute one or more embodiments or operations disclosed herein. In some embodiments, logic circuitry 110 may include hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP (Intellectual Property) cores" may be stored on a tangible, machine readable medium and supplied to various customers or manufacturing facilities to load into the fabrication machines that actually make the logic or processor. Some embodiments may be implemented, for example, using a machine-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

Figure 2B:
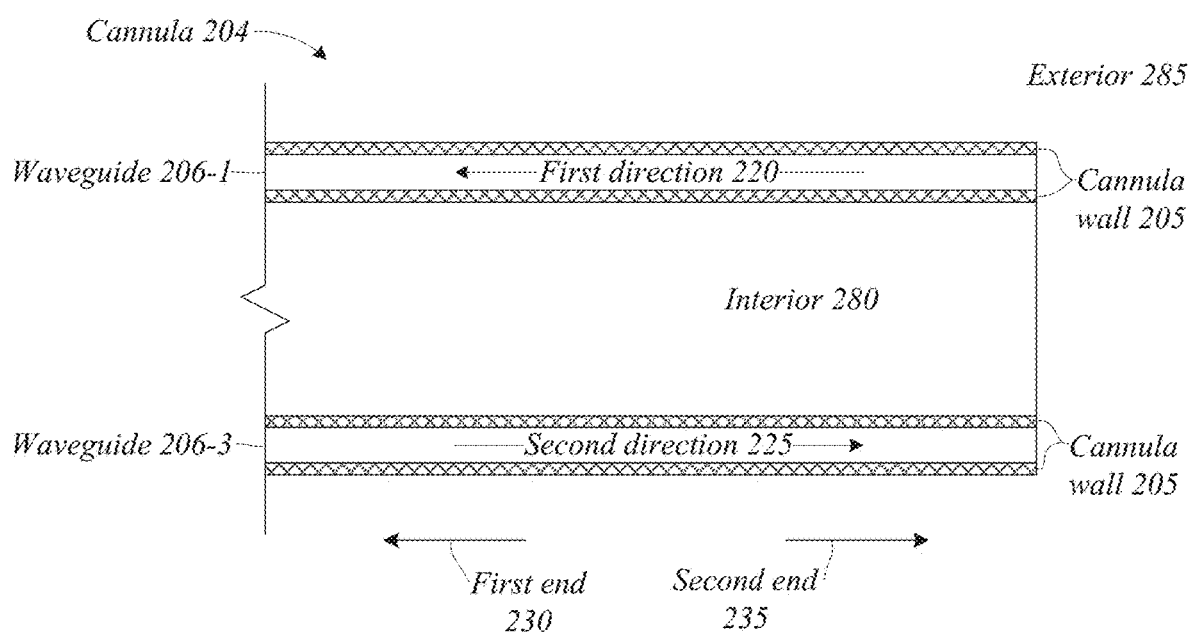

FIGS. 2A-2B illustrate embodiments of operating environments 200A and 200B that may be representative of various embodiments of a cannula. Operating environment 200A may include a front view of an end of a cannula 204. Operating environment 200B may include a cross-sectional side-view of cannula 204 along cut plane 210. In many embodiments, cannula 204 may be the same or similar to one or more other cannulas described herein, such as cannula 104. In various embodiments described herein, light may be received on the exterior 285 of cannula 204 via one or more of waveguides 206 to determine position and/or ambient lighting conditions of cannula 204. In some embodiments, light may be emitted on the exterior 285 of cannula 204 via one or more of waveguides 206 to determine a position of cannula 204 and/or ambient lighting or illumination. Embodiments are not limited in this context.

In many embodiments, light may travel in either the first direction 220 or the second direction 225 in each of the waveguides 206-1, 206-2. However, for simplicity first and second directions 220, 225 are only illustrated with respect to one waveguide. In some embodiments, light that enters one or more of waveguides 206 at their second end 235, which may be, for example, a distal end of the surgical instrument, may travel in the one or more of waveguides 206 in the first direction 220, i.e, from the distal end toward the proximal end. In various embodiments, light that exits one or more of waveguides 206 at their second end 235 may travel in the one or more of waveguides 206 in the second direction 225. As will be described in more detail below, such as with respect to FIG. 4B, when light travels in both directions in a waveguide, a beam splitter may be used to filter out light traveling in a specific direction, such as for the detection of light by transducer 108. In various embodiments, cannula 204 may include any number/configuration of waveguides 206. In the illustrated embodiments, cannula 204 includes waveguides 206-1, 206-2, 206-3, 206-4.

In some embodiments, each of waveguides 206 may emit and/or receive light on the exterior 285 of cannula 204. In other words, light may exit and/or enter one or more of waveguides 206 at their second end 235 on the exterior 285 of cannula 204. In some such embodiments, detection of received light may enable surgical instrument 102 to determine one or more parameters associated with an ocular surgery. For instance, waveguide 206-1 may emit light and the amount of emitted light that is reflected back into waveguide 206-1 and detected, such as by transducer 108, may be used to determine an amount of illumination inside an eye.

As previously mentioned, at least a portion of one or more waveguides (e.g., waveguides 206) may be embedded, or at least coupled, to a cannula (e.g., cannula 204). In the illustrated embodiment, waveguides 206 may be embedded in cannula wall 205. In one or more embodiments, transducer 108 may be located proximate the first end 230 of one or more of waveguides 206. In some embodiments, transducer 108 may be coupled to one or more waveguides. In some such embodiments, transducer 108 may be coupled to the one or more waveguides via a beam splitter. In various embodiments, one or more of waveguides 206 may be coupled to a light source, such as for illumination purposes or determining cannula location. In various such embodiments, the light source may be coupled to the one or more waveguides proximate the first end 230. In other embodiments, the light source may be coupled to or disposed on/in cannula 204. For example, the light source may be embedded in cannula wall 205.

In one or more embodiments, light exiting the light source may travel along an illumination path. In one or more such embodiments, light traveling in the second direction 225 may travel along the illumination path (e.g., in a distal direction toward a distal tip of the surgical instrument) and light traveling in the first direction 220 may travel retrograde to the illumination path (e.g., entering at the distal tip of the surgical instrument and traveling therefrom in a proximal direction). In some embodiments, light traveling in the first direction 220 may be referred to or include light traveling retrograde in a waveguide. For example, light may travel retrograde in a waveguide comprising an illumination nanofiber. In such examples, the light travelling retrograde in the illumination nanofiber may be detected by transducer 108.

Figure 3A:
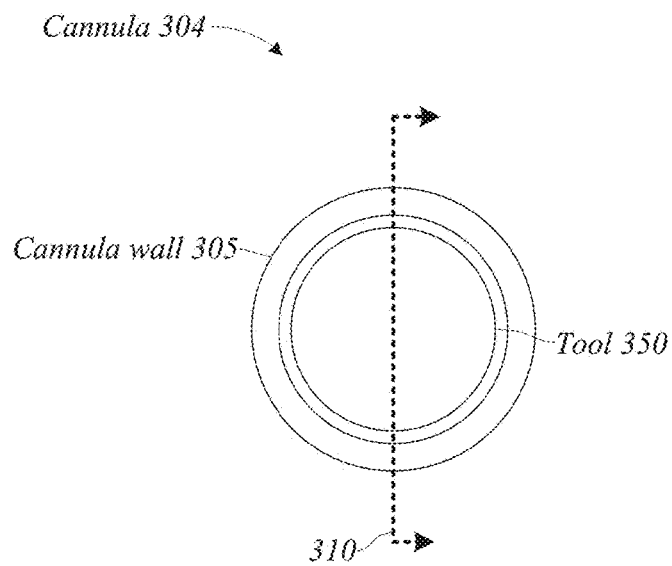
FIGS. 3A-3B illustrate an exemplary cannula according to one or more embodiments described herein.
Figure 3B:
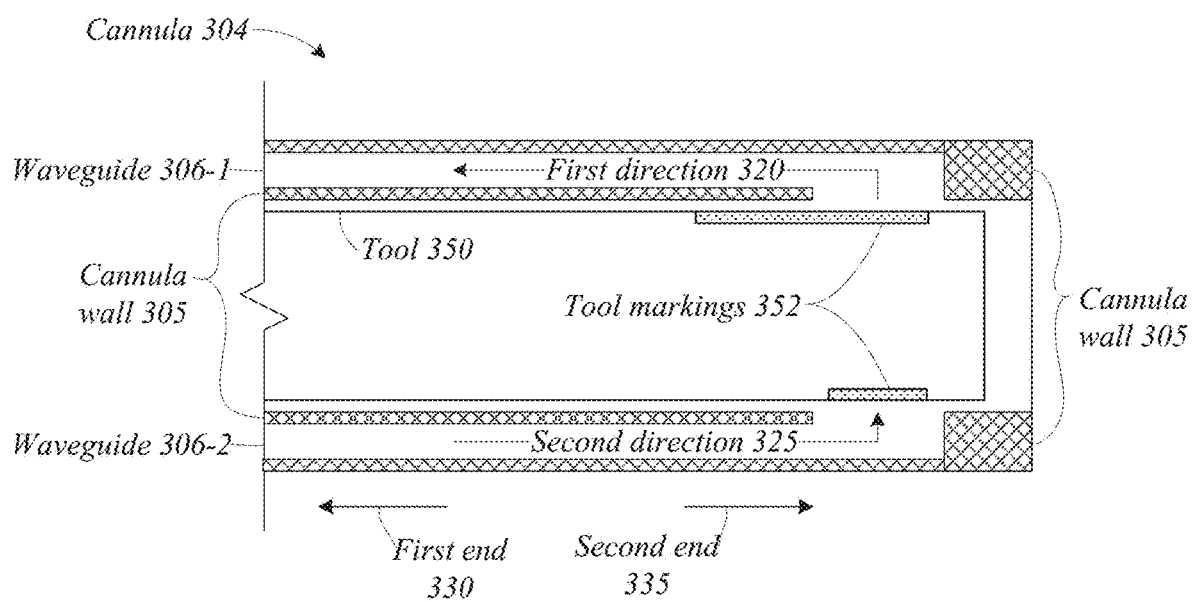

FIGS. 3A-3B illustrate embodiments of operating environments 300A and 300B that may be representative of various embodiments of a cannula. Operating environment 300A may include a front view of an end of a cannula 304. Operating environment 300B may include a cross-sectional view of cannula 304 along cut plane 310. In many embodiments, cannula 204 may be the same or similar to one or more other cannulas described herein, such as cannula 104. In various embodiments described herein, light may be emitted and/or received on the interior (see, e.g., interior 280 of FIG. 2B) of cannula 304 via one or more of waveguides 306 to determine one or more of a position and identity of a tool 350. Embodiments are not limited in this context.

In many embodiments, light may travel in either the first direction 320 or the second direction 325 in each of the waveguides 306-1, 306-2. However, for simplicity first and second directions 320, 325 are only illustrated with respect to one waveguide. In some embodiments, cannula 304 may include a set of waveguides that are the same or similar to waveguides 206 in addition to waveguides 306. In other words, a first set of waveguides may emit and/or receive light on the exterior 285 of cannula 304 while a second set of waveguides may emit and/or receive light on the interior 280 of cannula 304. For instance, light may be emitted/received on the exterior of cannula 304 for illumination control and cannula position purposes and light may be emitted/received on the interior of cannula 304 for tool identification and position purposes. As will be described in more detail below (see, e.g., FIG. 4B), when light travels in both directions in a waveguide, a beam splitter may be used to filter out light traveling in a specific direction, such as for the detection of light by transducer 108.

In some embodiments, light that enters one or more of waveguides 306 at their second end 335 may travel in the one or more of waveguides 306 in the first direction 320. In various embodiments, light that exits one or more of waveguides 306 at their second end 335 may travel in the one or more of waveguides 306 in the second direction 225. As will be described in more detail below, such as with respect to FIG. 4B, when light travels in both directions in a waveguide, a beam splitter may be used to filter out light traveling in a specific direction, such as for the detection of light by transducer 108. In various embodiments, cannula 304 may include any number/configuration of waveguides 306. In the illustrated embodiments, cannula 304 includes waveguides 306-1, 306-2.

In some embodiments, each of waveguides 306 may emit and/or receive light on the interior (see e.g., interior 280 of FIG. 2B) of cannula 304. In other words, light may exit and/or enter one or more of waveguides 306 on the interior of cannula 304, at the second end 335. In some such embodiments, detection of received light may enable surgical instrument 102 to determine one or more parameters associated with an ocular surgery. For instance, waveguide 306-1 may emit light and the amount of emitted light that is reflected back into waveguide 206-1 and detected, such as by transducer 108, may be used to read tool markings 352 on tool 350. In may embodiments, tool markings 352 may be read to determine one or more of an identity and position/location of tool 350. For example, tool markings 352 may be used to identify tool 350 as a cutter that is located inside an eye.

As previously mentioned, at least a portion of one or more waveguides (e.g., waveguides 306) may be embedded, or at least coupled, to a cannula (e.g., cannula 204). In the illustrated embodiment, waveguides 306 may be embedded in cannula wall 305. In one or more embodiments, transducer 108 may be located proximate the first end 330 of one or more of waveguides 306. In some embodiments, transducer 108 may be coupled to one or more waveguides. In some such embodiments, transducer 108 may be coupled to the one or more waveguides via a beam splitter. In various embodiments, one or more of waveguides 306 may be coupled to a light source, such as for illumination purposes or determining cannula location. In various such embodiments, the light source may be coupled to the one or more waveguides proximate the first end 330. In other embodiments, the light source may be coupled to or disposed on/in cannula 304. For example, the light source may be embedded in cannula wall 305.

In one or more embodiments, light exiting the light source may travel along an illumination path. In one or more such embodiments, light traveling in the second direction 325 may travel along the illumination path and light traveling in the first direction 320 may travel retrograde to the illumination path. In various embodiments, when tool markings 352 are within the illumination path, they may be read by surgical instrument 102. In some embodiments, light traveling in the first direction 320 may be referred to or include light traveling retrograde in a waveguide. For example, light may travel retrograde in a waveguide comprising an illumination nanofiber. In such examples, the light travelling retrograde in the illumination nanofiber may be detected by transducer 108.

Figure 4A:
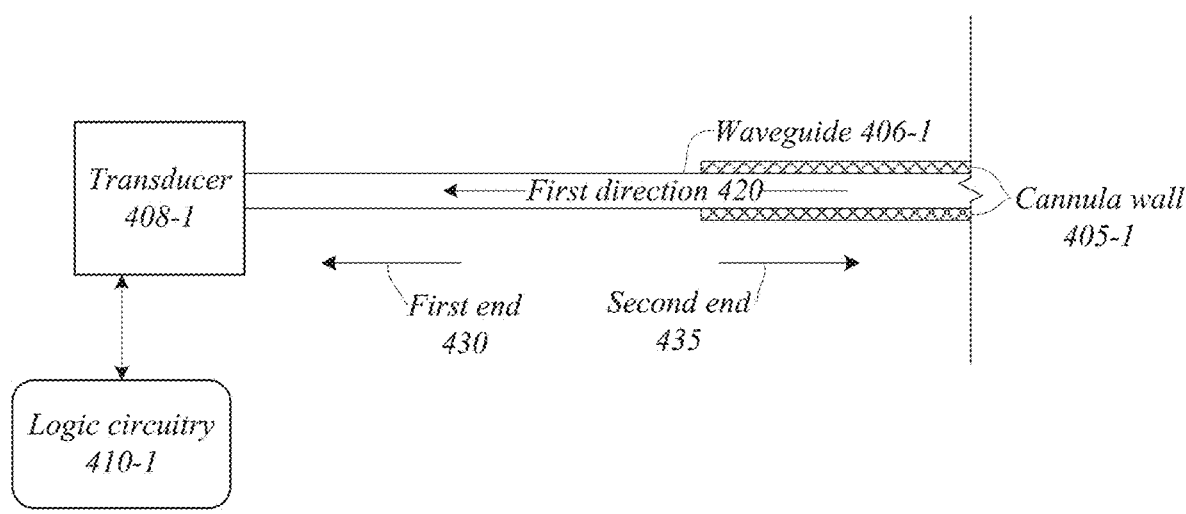
FIG. 4A illustrates a portion of an exemplary surgical instrument according to one or more embodiments described herein.

FIG. 4A illustrates an embodiment of an operating environment 400A that may be representative of various embodiments. Operating environment 400A may include waveguide 406-1, transducer 408-1, and logic circuitry 410-1. In various embodiments, one or more components of operating environment 400A may be the same or similar to one or more other components described herein. In the illustrated embodiments, a portion of waveguide 406-1 may be embedded in cannula wall 405-1. In one or more embodiments described herein, logic circuitry 410-1 may determine one or more parameters associated with ocular or ophthalmic surgery based on light. For instance, transducer 408-1 may detect light traveling within waveguide 406-1 in first direction 420 (e.g., entering a distal tip of the surgical instrument and traveling from the distal end to the proximal end), and logic circuitry 410-1 may determine one or more parameters associated with ocular surgery based on the light detected by the transducer 408-1. In some embodiments, waveguide 406-1 may be the same or similar to one or more other waveguides described herein. Embodiments are not limited in this context.

Figure 4B:
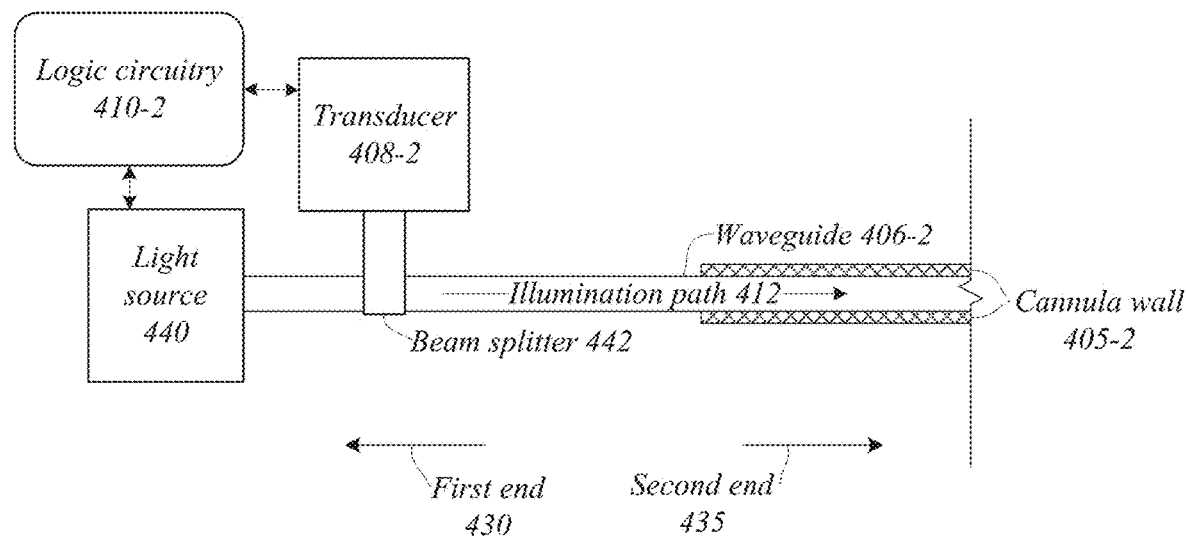
FIG. 4B illustrates a portion of an exemplary surgical instrument according to one or more embodiments described herein.

FIG. 4B illustrates an embodiment of an operating environment 400B that may be representative of various embodiments. Operating environment 400B may include waveguide 406-2, transducer 408-2, logic circuitry 410-2, light source 440, and beam splitter 442. In various embodiments, one or more components of operating environment 400A may be the same or similar to one or more other components described herein. In the illustrated embodiments, a portion of waveguide 406-2 may be embedded in cannula wall 405-2. In one or more embodiments described herein, logic circuitry 410-2 may determine one or more parameters associated with ocular or ophthalmic surgery based on light generated by light source 440. For instance, light source 440 may generate light that travels in waveguide 406-2 along illumination path 412. In such instances, the light may exit waveguide 406-2, reflect off markings on a tool, and enter waveguide 406-2. In further such instances, beam splitter 442 may filter out light traveling within waveguide 406-2 retrograde to illumination path 412 (e.g., the light that enters waveguide 406-2) such that it can be detected by transducer 408-2, and logic circuitry 410-1 may determine one or more parameters associated with ocular surgery based on the light detected by the transducer 408-2. In some embodiments, waveguide 406-2 may be the same or similar to one or more other waveguides described herein. Embodiments are not limited in this context.

Figure 5A:
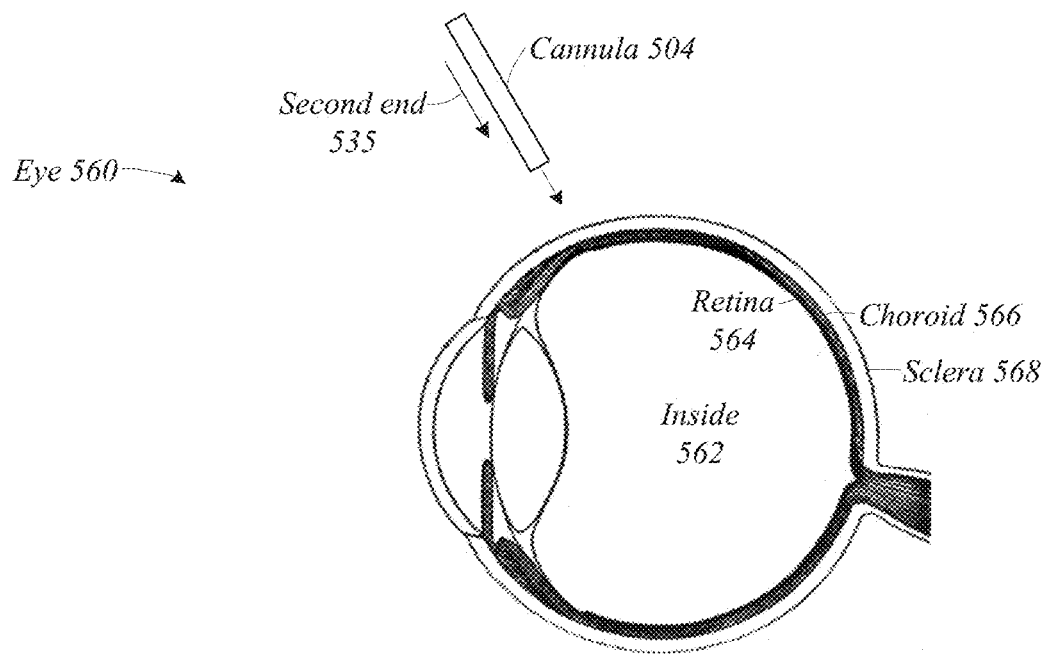
FIGS. 5A-5B illustrate a procedure with an exemplary surgical instrument according to one or more embodiments described herein.
Figure 5B:
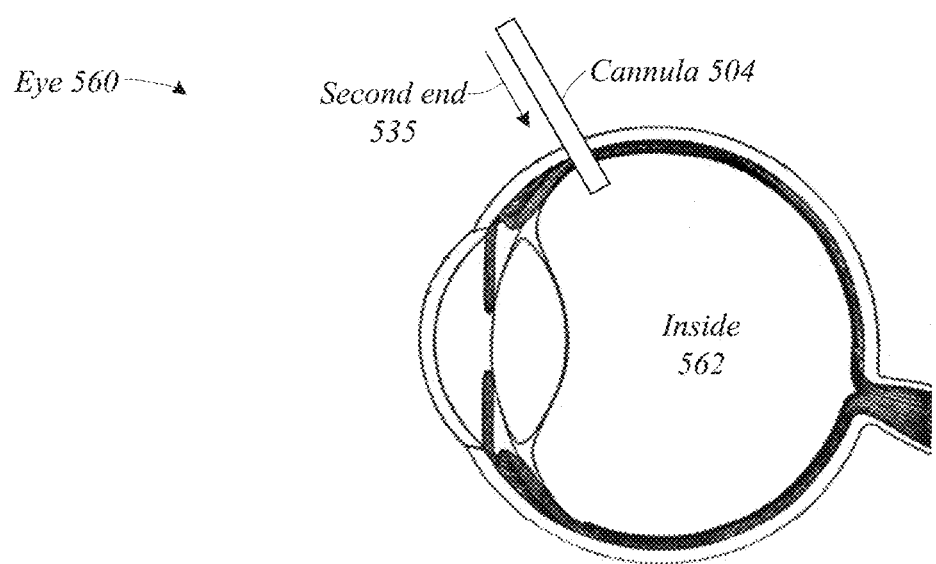

FIGS. 5A-5B illustrate embodiments of operating environments 500A and 500B that may be representative of an exemplary procedure performed with one or more surgical instruments, or components thereof, described herein. Operating environment 500A may include cannula 504 located outside of eye 560. Operating environment 500B may include cannula 504 located on the inside 562 of eye 560. In many embodiments, one or more components of operating environments 500A, 500B may be the same or similar to one or more other components described herein. In various embodiments described herein, light may be emitted and/or received on the exterior of cannula 504 via one or more of waveguides to determine one or more of a position of cannula 504 and an amount of illumination or ambient light is present proximate the second end 535 of cannula 504. For instance, an amount of illumination of the inside 562 of eye 560 may be determined. In some embodiments, a position of cannula 504 may be determined. For example, whether cannula 504 is located between the sclera 568 and choroid 566 or on the inside 562 may be determined based on an amount of detected light. Embodiments are not limited in this context. For example, a light source may be activated to send light through the surgical instrument from the proximal end to the distal end, such that light is emitted from the distal end. The emitted light is reflected back into the distal end of the surgical instrument (for example, reflected off of the retina or other tissue) and travels retrograde, i.e., proximally, through the waveguide to the transducer. The transducer determines the amount of reflected light. If the distal tip of the surgical instrument (e.g., infusion cannula) is in the suprachoroidal space (e.g., bordered by opaque sclera on one side and dense melanin pigment in the choroid on the other side), the amount of reflected light will be significantly lower than if the distal tip is fully inserted into the inside 562 of the eye. Thus, by detecting the amount of light, the position of the distal tip can be determined. For example, it can be determined if an infusion cannula is in the inside of the eye prior to activating infusion, in order to avoid detrimental infusion into the suprachoroidal space. In another example, the light source may be from another source, such as a microscope, whereby the light is sent into the eye and reflected into the distal end of the surgical instrument.

Figure 6A:
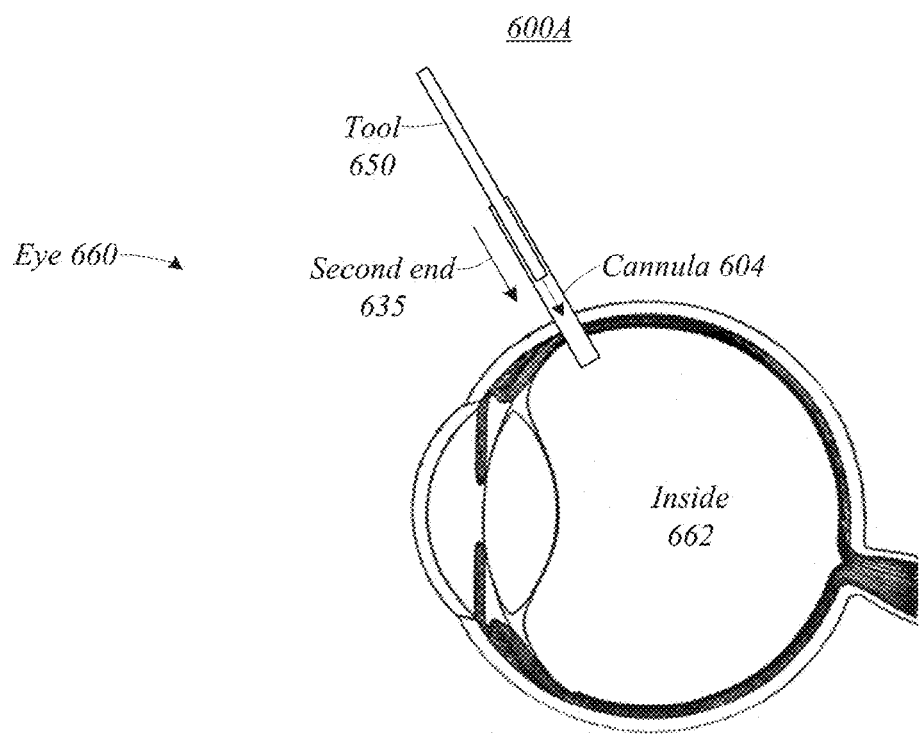
FIGS. 6A-6B illustrate a procedure with an exemplary surgical instrument according to one or more embodiments described herein.
Figure 6B:
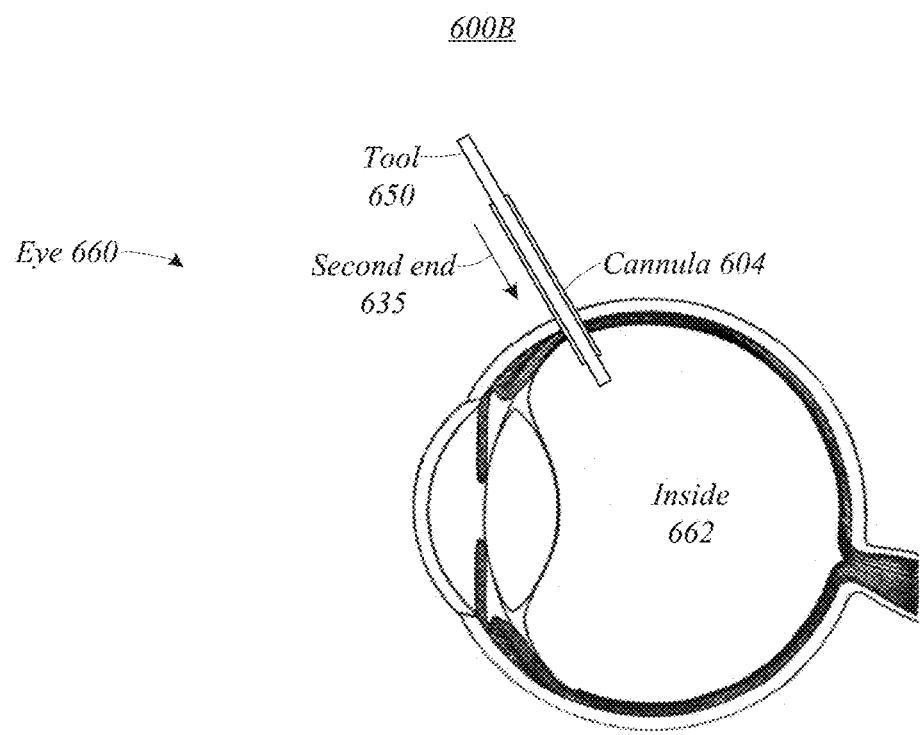

FIGS. 6A-6B illustrate embodiments of operating environments 600A and 600B that may be representative of an exemplary procedure performed with one or more surgical instruments, or components thereof, described herein. Operating environment 600A may include cannula 604 located inside 662 of eye 660 and tool 650 located outside of eye 660. Operating environment 600B may include cannula 604 located on the inside 662 of eye 660 and tool 650 located inside 662 of eye 660. In many embodiments, one or more components of operating environments 600A, 600B may be the same or similar to one or more other components described herein. In various embodiments described herein, light may be emitted and/or received on the interior of cannula 604 via one or more of waveguides to determine one or more of a position or identity of tool 650. For instance, one or more markings on tool 650 may be read based on light reflected off the markings. In such instances, the markings may include a bar code for identity and/or a position gauge for location. In some embodiments, a position gauge may include a plurality of rings and the position of the tool 650 may be determined based on the number of detected rings. Embodiments are not limited in this context.

The following examples pertain to further embodiments, from which numerous permutations and configurations will be apparent.

Examples 1 is an apparatus for use in ocular surgery, comprising: a surgical instrument comprising at least a portion of a waveguide, the surgical instrument having a proximal end and a distal end; a transducer to detect light entering the distal end of the surgical instrument and traveling in a proximal direction in the waveguide; and logic, at least a portion of the logic implemented in circuitry communicatively coupled with the transducer, the logic to determine at least one parameter associated with the ocular surgery based on the light detected by the transducer.

Example 2 includes the subject matter of Example 1, wherein the surgical instrument comprises a cannula Example 3 includes the subject matter of Example 1, wherein the waveguide comprises an illumination nanofiber.

Example 4 includes the subject matter of Example 3, wherein the waveguide includes at least a portion of an illumination path of a light source and the transducer utilizes a beam splitter in the illumination path to detect the light traveling in the proximal direction in the illumination nanofiber.

Example 5 includes the subject matter of Example 4, wherein the light source generates light traveling in a distal direction in the waveguide, toward the distal end of the surgical instrument.

Example 6 includes the subject matter of Example 1, wherein the at least one parameter associated with ocular surgery comprises whether the surgical instrument is located inside an eye.

Example 7 includes the subject matter of Example 6, wherein the logic is configured to determine whether the distal end of the surgical instrument is located inside the eye based on an amount of light detected by the transducer.

Example 8 includes the subject matter of Example 2, wherein the at least one parameter associated with ocular surgery comprises whether the cannula is located inside an eye.

Example 9 includes the subject matter of Example 8, wherein the logic is configured to determine whether the cannula is inside the eye based on an amount of light detected by the transducer.

Example 10 includes the subject matter of Example 1, wherein the at least one parameter associated with ocular surgery comprises an identity of a second surgical instrument inserted into the cannula.

Example 11 includes the subject matter of Example 10, wherein the logic is configured to read a bar code located on the second surgical instrument based on the light detected by the transducer to determine the identity of the second surgical instrument inserted into the cannula.

Example 12 includes the subject matter of Example 1, wherein the at least one parameter associated with ocular surgery comprises an amount of illumination within an eye.

Example 13 includes the subject matter of Example 12, wherein the logic is configured to:
compare the amount of illumination within the eye to a threshold; and
perform an action when the amount of illumination within the eye exceeds the threshold.

Example 14 includes the subject matter of Example 13, comprising a light source and wherein the action comprises adjusting the light source.

Example 15 includes the subject matter of Example 13, wherein the action comprises generating an alert.

Example 16 includes the subject matter of Example 1, the surgical instrument comprising an infusion cannula.

Example 17 includes the subject matter of Example 1, wherein the portion of the waveguide comprised in the surgical instrument is embedded in a wall of the surgical instrument.

Example 18 includes the subject matter of Example 1, wherein the waveguide comprises an optical fiber array.

Example 19 is a method comprising one or more operations performed by an apparatus as described in any of Examples 1 to 18.

Example 20 is an apparatus for surgical use, comprising: a surgical instrument comprising at least a portion of a waveguide, the waveguide comprising first end and a second end, wherein the portion of the waveguide is proximate the second end of the waveguide; a transducer to detect light traveling toward the first end of the waveguide; and logic, at least a portion of the logic implemented in circuitry communicatively coupled with the transducer, the logic to identify at least one parameter associated with ocular surgery based on the light traveling toward the first end of the waveguide.

Example 21 includes the subject matter of Example 20, the waveguide comprising an illumination nanofiber, wherein a light source generates light traveling toward the second end of the illumination nanofiber.

Example 22 includes the subject matter of Example 21, wherein the transducer utilizes a beam splitter in an illumination path of the light source to detect the light traveling toward the first end of the waveguide.

Example 23 includes the subject matter of Example 21, wherein the light source is coupled to the first end of the waveguide.

Example 24 includes the subject matter of Example 20, wherein the at least one parameter associated with ocular surgery comprises whether the surgical instrument is located inside an eye.

Example 25 includes the subject matter of Example 20, wherein the at least one parameter associated with ocular surgery comprises whether a tool is inside an eye.

Example 26 includes the subject matter of Example 20, wherein the at least one parameter associated with ocular surgery comprises an identity of a tool inserted via the surgical instrument.

Example 27 includes the subject matter of Example 20, the waveguide comprising an optical fiber array.

A method comprising one or more operations performed by an apparatus as described in any of Examples 20 to 27.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner, and may generally include any set of one or more limitations as variously disclosed or otherwise demonstrated herein.

The invention claimed is:
1. An apparatus for use in ocular surgery, comprising:
a surgical instrument comprising at least a portion of a waveguide, the surgical instrument having a proximal end and a distal end;

a transducer to detect light entering the distal end of the surgical instrument and traveling in a proximal direction in the waveguide; and logic, at least a portion of the logic implemented in circuitry communicatively coupled with the transducer, the logic to determine at least one parameter associated with the ocular surgery based on the light detected by the transducer;

wherein the surgical instrument comprises a cannula;

wherein the at least one parameter associated with ocular surgery comprises an identity of a second surgical instrument inserted into the cannula;

wherein the logic is configured to read a bar code located on the second surgical instrument based on the light detected by the transducer to determine the identity of the second surgical instrument inserted into the cannula;

wherein the at least a portion of a waveguide includes one or more waveguides that terminate on an exterior of the cannula and one or more waveguides that terminate on an interior of the cannula;

wherein light detected from the waveguides that terminate on the exterior of the cannula is used for determining parameters associated with an environment or location of the cannula including at least one additional parameter associated with whether the cannula is located inside an eye; and wherein light detected from the waveguides that terminate on the interior of the cannula is used for determining parameters associated with the second surgical instrument inserted into the cannula including determining the identity of the second surgical instrument inserted into the cannula.

2. The apparatus of claim 1, wherein the waveguide comprises an illumination nanofiber.

3. The apparatus of claim 2, wherein the waveguide includes at least a portion of an illumination path of a light source and the transducer utilizes a beam splitter in the illumination path to detect the light traveling in the proximal direction in the illumination nanofiber.

4. The apparatus of claim 3, wherein the light source generates light traveling in a distal direction in the waveguide, toward the distal end of the surgical tool.

5. The apparatus of claim 1, wherein the logic is configured to determine whether the distal end of the cannula is located inside the eye based on an amount of light detected by the transducer.

6. The apparatus of claim 1, wherein at least one additional parameter of the at least one parameter associated with ocular surgery comprises an amount of illumination within an eye.

7. The apparatus of claim 6, wherein the logic is configured to:
compare the amount of illumination within the eye to a threshold; and
perform an action when the amount of illumination within the eye exceeds the threshold.

8. The apparatus of claim 7, comprising a light source and wherein the action comprises adjusting the light source.

9. The apparatus of claim 7, wherein the action comprises generating an alert.

10. A method, comprising:
detecting light traveling in a first direction in a waveguide with a transducer, wherein at least a portion of the waveguide is included in a surgical instrument; and
determining at least one parameter associated with ocular surgery based on the light detected by the transducer;
wherein the surgical instrument is a first surgical instrument and comprises a cannula;
wherein the at least one parameter associated with ocular surgery comprises an identity of a second surgical instrument inserted into the cannula;
wherein the determining the at least one parameter comprises reading a bar code located on the second surgical instrument based on the light detected by the transducer to determine the identity of the second surgical instrument inserted into the cannula;
wherein the at least a portion of a waveguide includes one or more waveguides that terminate on an exterior of the cannula and one or more waveguides that terminate on an interior of the cannula;
wherein the method further comprises:
using light detected from the waveguides that terminate on the exterior of the cannula for determining parameters associated with an environment or location of the cannula including at least one additional parameter associated with whether the cannula is located inside an eye;
using light detected from the waveguides that terminate on the interior of the cannula for determining parameters associated with the second surgical instrument inserted into the cannula including determining the identity of the second surgical instrument inserted into the cannula.

11. The method of claim 10, wherein at least one additional parameter of the at least one parameter associated with ocular surgery comprises whether a second surgical instrument is located inside an eye.

12. The method of claim 10, wherein at least one additional parameter of the at least one parameter associated with ocular surgery comprises an amount of illumination within an eye.

* * * * *